(12) United States Patent
Braun et al.

(10) Patent No.: US 7,476,658 B2
(45) Date of Patent: Jan. 13, 2009

(54) CONJUGATE FOR TREATING PROKARYOTIC INFECTIONS

(75) Inventors: Klaus Braun, Sandhausen (DE); Isabell Braun, Cölbe-Bürgein (DE); Jürgen Debus, Heidelberg (DE); Rüdiger Pipkorn, Heidelberg (DE); Waldemar Waldeck, Laudenbach (DE)

(73) Assignee: Deutsches Krebsforschungszentrum Stiftung des Offentlichen Rechts (DE)

( * ) Notice: Subject to any disclaimer, the term of this patent is extended or adjusted under 35 U.S.C. 154(b) by 374 days.

(21) Appl. No.: 10/501,962

(22) PCT Filed: Jan. 17, 2003

(86) PCT No.: PCT/DE03/00124

§ 371 (c)(1),
(2), (4) Date: Oct. 4, 2004

(87) PCT Pub. No.: WO03/059392

PCT Pub. Date: Jul. 24, 2003

(65) Prior Publication Data

US 2005/0222008 A1    Oct. 6, 2005

(30) Foreign Application Priority Data

Jan. 18, 2002  (DE) ................ 102 01 862

(51) Int. Cl.
*A61K 31/70* (2006.01)
*C07H 21/04* (2006.01)
*C12N 5/00* (2006.01)
*C12Q 1/68* (2006.01)

(52) U.S. Cl. ............... 514/44; 536/24.1; 536/24.5; 435/6

(58) Field of Classification Search ............ None
See application file for complete search history.

(56) References Cited

U.S. PATENT DOCUMENTS 6,548,651 B1 * 4/2003 Nielsen et al. ......... 536/23.1
6,821,948 B1 * 11/2004 Braun et al. .............. 514/2

FOREIGN PATENT DOCUMENTS

| WO | WO 96/03519 | 2/1996 |
|---|---|---|
| WO | WO 96/11205 | 4/1996 |
| WO | WO 98/52614 | * 11/1998 |
| WO | WO 99/65506 | 12/1999 |
| WO | WO 00/68265 | 11/2000 |
| WO | WO-01/05432 A2 | 1/2001 |
| WO | WO-03/006065 A2 | 1/2003 |

OTHER PUBLICATIONS

Bernhardt et al. Research in Microbiology, vol. 153: 493-501, 2002.*
Oki et al., Gene vol. 197:137-145, Apr. 16, 1997.*
Sambrook, et al., Molecular Cloning, A Laboratory Manual (Second Edition), Cold Spring Harbor Laboratory Press, pp. 7.84-7.87 (1989).
Nielsen, et al., Sequence Selctive Recognition of DNA by Strand Displacement with a Thymine-Substiuted Polyamide, Science, vol. 254, 1497-1500, (Dec. 1991).
R.B. Merrifield, Solid Phase Peptide Synthesis I. The Synthesis of a Tetrapeptide, vol. 85, 2148-2151 (1963).
Good, et al., "Batericidal antisense effects of peptide-PNA conjugates," Nature Biotechnology, vol. 19, Apr. 2001, 360-364.
Nielsen, Peter "Peptide nucleic acids as therapeutic agents," http://biomednet.com/elecref/095944OX00900353.
Braun, et al., A biological tansporter for the delivery of Peptide Nucleic Acids (PNAs) to the Nuclear Compartment of Living Cells; www.idealibrary.com.
Good, et al., "Bacterial antisense effects of peptide-PNA conjugates," Nature Biotechnology, vol. 19, No. 4, pp. 360-364 (Apr. 2001).
Good, et al., "Antisense inhibition of gene expression in bacteria by PNA targeted to mRNA," Nature Biotechnology, Apr. 16, 1998, pp. 355-358.
Tang, et al., "A cyclic Antimicrobial Peptide Produced in Primate Leukocytes by the Ligation of Two Truncated Defensins," Science, vol. 286, Oct. 15, 1999.
Hisako, et al., "Synthesis and characterization of bacterial oligopeptides designed on the basis of an insect anti-bacterial peptide," Biochemical Journal, 338, 29-33 (1999).
Periathamby, et al., "Large-scale synthesis and functional elements for the antimicrobial activity of defensins," Biochemical Journal, 347, 633-641 (2000).
Yu, et al., "Engineered Salt-insensitve Defensins with end-to-end circularized structures," The Journal of Biological Chemistry, (2000).
Pipkorn, et al., "Peptide Carrier for Efficient Drug Transprot into Living Cells," American Peptide Society, 931-932 (2001).

* cited by examiner

*Primary Examiner*—Sean R McGarry
(74) *Attorney, Agent, or Firm*—Kelly K. Reynolds; Intellectual Property/Technology Law; Steven J. Hultquist

(57) ABSTRACT

The invention relates to a conjugate for treating prokaryotic infections from a transport mediator penetrating the prokaryotic cell membrane and a desired compound to be introduced into the prokaryote and directed thereagainst, which compound is preferably a peptide nucleic acid (PNA) directed against a gene of the prokaryote giving antibiotic resistance.

11 Claims, 15 Drawing Sheets

Figure 4:
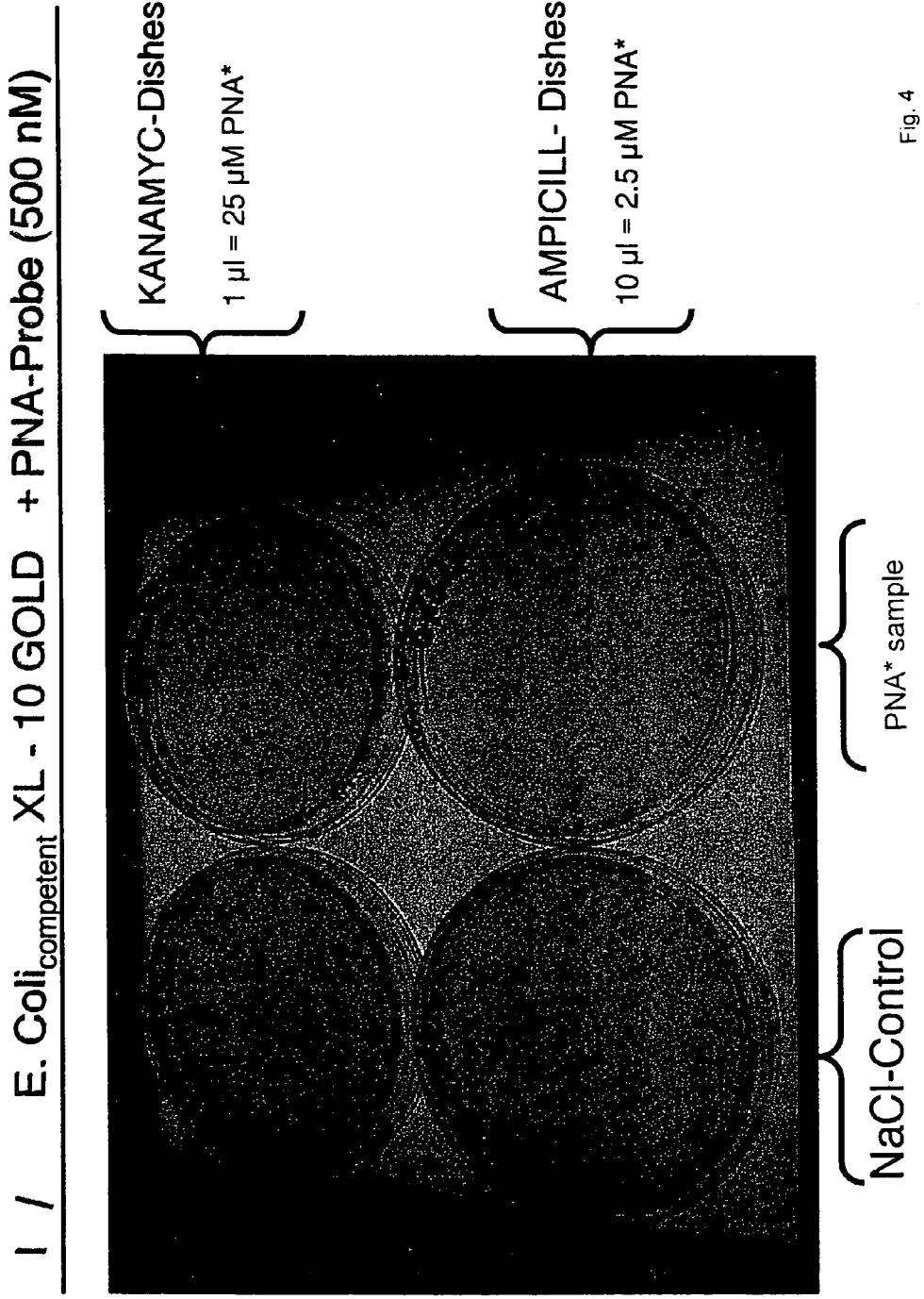

Strategies:

Defhuman —S⌒S— Glyc ⋯⋯ PNA⋯⋯ specific to bacterial membranes

+ anti-gene strategy directed specifically against bacterial genes

→ combined 'dual strategy'

Fig. 1

Genome site of action – anti-gene PNA

```
DEFINITION   Cloning vector pBR322, complete genome.
ACCESSION    J01749 - Genbank
KEYWORDS     ampicillin resistance; beta-lactamase; cloning vector; drug
             resistance protein; origin of replication; plasmid;
SOURCE       Cloning vector pBR322.
ORGANISM     Cloning vector pBR322
             artificial sequence; vectors.
```

```
TTCTCATGTT TGACAGCTTA TCATCGATAA GCTTTAATGC GGTAGTTTAT CACAGTTAAA        60
TTGCTAACGC AGTCAGGCAC CGTGTATGAA ATCTAACAAT GCGCTCATCG TCATCCTCGG       120
CACCGTCACC CTGGATGCTG TAGGCATAGG CTTGGTTATG ACGGTACTGC CGGGCCTCTT      180
GCGGGATATC GTCCATTCCG ACAGCATCGC CAGTCACTAT GGCGTGCTGC TAGCGCTATA      240
TGCGTTGATG CAATTTCTAT GCGCACCCGT TCTCGGAGCA CTGTCCGACC GCTTTGGCCG      300
CCGCCCAGTC GCTGTCGGTT CGTAGTTGG AGCCACTATC GACTACGCGA TCATGCGCAC      360
CACACCCGTC CTGTGGATCC TCTACGCCGG ACGCATCGTG GCCGGCATCA CCGGCGCCAC      420
AGGTGCGGTT GCTGGCGCCT ATATCGCCGA CATCACCGAT GGGGAAGATC GGGCTCGCCA      480
CTTCGGGCTC ATGAGCGCTT GTTTCGGCGT GGGTATGGTG GCAGGCCCCG TGGCCGGGGG      540
ACTGTTGGGC GCCATCTCCT TGCATGCACC ATTCCTTGCG GCGGCGGTGC TCAACGGCCT      600
``` anti-gene PNA

HOOC-TAC TTT AGA TTG TTA-NH$_2$

Fig. 2

Alignments Holin-Protein (Phagen) - *Transportprotein* product="probable holin" (GMSE-1)
[Endosymbiont bacteriophage may influence susceptibility to trypanosome infection in tsetse, Dale and Young]
protein_id="AAG50251.1"
db_xref="GI:12276078"
translation="MPCLIHLVGWGSSPGSALIREQAIGAGLAAWMTCLRGRYLGRGWRKTTFDAAICALIAWF
ARDGLALVGIDNQFSYLSSIIVGYLGNDYLGALLRRRLEKKS GESNAPQ product="holin protein" (Listeria innocua)
protein_id="CAA61518.1"
translation="MMKMEFGKELLVYMTFLVVVTPVFVQAIKKTELIPSKWLPTVSILVGAILGALATSLDGSG
SLATMIWAGALAGAGGTGLFEQFTNRAKKYGKDD product="holin" (bacteriophage 80 alpha)
specific_host="Staphylococcus aureus RN450
function="makes hole in membrane"
protein_id="AAB39698.1"
db_xref="GI:1763242"
translation="MDINWKLRFKNKAVLTGLVGALFVFIKQVTDLFGLDLSTQLNQASAIIGAILTLLTGIGVIT
DPTSKGVSDSSIAQTYQAPRDSKKEEQQVTWKSSQDSSLTPELSAKAPKEYDTSQPFTDASNDVGFDVN
EYHHGGGDNASKIN product="holin" (Staphylococcus bacteriophage phi 11)
note="ORF3; structural homologue of holin"
protein_id="AAA99522.1"
db_xref="GI:511841"
translation="MDINWKLRFKNKAVLTGLVGALFVFIKQVTDLFGLDLSTQLNQASAIIGAILTLLTGIGVIT
DPTSKGVSDSSIAQTYQAPRDSKKEEQQVTWKSSQDSSLTPELSAKAPKEYDTSQPFTDASNDVGFDVN
EYHHGGGDNASKIN product="putative holin 1" (Streptococcus pneumoniae bacteriophage MM1)
function="lysis protein"
protein_id="CAC48114.1"
db_xref="GI:15074937"
translation="MKIEFFNFLRSVIQTEDGLVLYALALIVSMEIIDFVTGTIAAIINPDIEYKSKIGINGLLRKISGV
LLLMILIPASVLLPEKTGFAFLYSICLGYIAFTFQSLIENYRKLKGNVTLFQPIVKVFQRLLEKDDDTKKGE gene="orf87a" (Streptococcus thermophilus bacteriophage Sfi21)
product="holin"
protein_id="CAA64941.1"
db_xref="GI:2292749"
translation="MKKRKKKMINFKLRLQNKATLVALISAVFLMLQQFGLHVPNNIQGINTLVGILVILGIITDP
TTKGIADSERALSYIQPLDDKEVY gene="hol500" (Bacteriophage A500);(Listeria monocytogenes)
protein_id="CAA59363.1"
/db_xref="GI:853745"
/translation="MMKMEFGKELLVYMTFLVVVTPVFVQAIKKTELIPSKWLPTVSILVGAILGALATSLDGSG
SLATMIWAGALAGAGGTGLFEQFTNRAKKYGKDDK product="holin" (Bacteriophage PL-1)
protein_id="BAA96748.1"
translation="MQNELLQVLAIAFVIAPITTGFTEIFKRYTPAEGKLLPVLSIGTG
ILLACVWAMAFGHLPLIGAYALAGMLSGLASVGVYQIVKPNEEVK

Fig. 3 gene="lydA" (Bacteriophage P1) (enterobacteriae)
codon_start=1
product="holin"
protein_id="CAA61014.1"
db_xref="GI:974764"
translation="MLDTQELAPVAIALLLSVIGGIGTFLMDVRDGRQSGNLLGLVTEIFVAVTAGAVAYLLGQH
EGWELSITYLMVTIASNNGHEVISGMKRVNIDSILNVLTSLVKKGGGK gene="S" (Bacteriophage H-19B)
note="similar to Bacteriophage 21 lysis gene S, encoded by GenBank Accession Number M65239" /
product="putative holin protein"
protein_id="AAD04658.1"
db_xref="GI:2668771"
translation="MEKITTGVSYTTSAVGTGYWLLQLLDKVSPSQWVAIGVLGSLLFGLLTYLTNLYFKIREDR
RKAVRGE gene="hol" (Bacteriophage A118)
function="forms unspecific lesions into cytoplasmic membrane prior to lysis"
specific_host="Listeria monocytogenes"
note="ORF24; two products may be translated from this gene (hol-96 and hol-93)"
product="holin"
protein_id="CAB53810.1"
db_xref="GI:5823622"
translation="MIEMEFGKELLVYMTFLVVVTPVFVQAIKKTELVPSKWLPTVSILIGAILGALATFLDGSGS
LATMIWAGALAGAGGTGLFEQFTNRSKKYGEDDK gene="Hol" (Lactobacillus casei bacteriophage A2)
product="putative holine"
protein_id="CAB87385.1"
db_xref="GI:7573220"
translation="MKINWKVAVLSVKFWLALVPAALLVVQTAAAVFGYNWDFANLGKELTAVINAVFALLTI
VGVAVDPTTEGVSDSQQALAYPALITTKAAKIKSLEDQIKALQADKAADQATSAASEVVPETSSAAPAE
SAPESVAPVASEEVK gene="Hol" (Lactobacillus bacteriophage phig1e)
product="holin"
protein_id="CAA66751.1"
db_xref="GI:1926366"
translation="MDIITSLNLATAGELALISFFIGVIVQAIKKTGKVKNTYLPFISMGIGILAGLAAVVVTKDTN
YLNGAVAGLIVGAATSGLTDGLSVGTSAVTTAKATKDAAKTAAITQAVLNSINTTKSSDTTQVANTSN
TEGGSTSETQK product="holin" (Lactobacillus delbrueckii subsp. lactis bacteriophage LL-H)
protein_id="AAC00556.1"
db_xref="GI:623083"
translation="MTLIDWFNLIVAIGTIALAVVASVYVHLKAKIDTKTAAGKAFDLVGKLAVWAVNEAEHSQ
DGGAAKREFAAKLISDQLKAKGITGIDEKMVYGAVETAWKEA IENVK product="holin protein" (Lactococcus phage c2)
protein_id="AAD20611.1"
db_xref="GI:4426933"
translation="MIETLRAIGLVVFMQLLSLALEFIDTGTLKPSVRKRIAVELMVL gene="hol" (bacteriophage phiAM2)
note="hydrophobic pore-forming protein"
product="holin"
protein_id="AAG24367.1"
db_xref="GI:10880732"
translation="MFFNNKFYNVIKWAVLTALPALSVFIGVIGKAYGWGGTDLAIITLNAFTVFLGTLAGVSAV
KYNSQPNDTKENK

Fig. 3 product="holin"
protein_id="AAG24367.1"
translation="MFFNNKFYNVIKWAVLTALPALSVFIGVIGKAYGWGGTDLAIITLNAFTVFLGTLAGVSAV
KYNSQPNDTKENK product="holin" (Bacteriophage Tuc2009)
protein_id="AAA32614.1"
db_xref="GI:496282"
translation="MNQINWKLRLKSKAFWLALLPALFLLIQAIGAPFGYKWDFVILNQQLAAVVNAAFALLAI
VGVVADPTTSGLGDSDRVLNKDKSEENK product="holin" (Bacteriophage TPW22)
function="formation of non-specific lesions in the cytoplasmic membrane"
protein_id="AAF12704.1"
db_xref="GI:6465904"
translation="MNQINWKLRLKSKAFWLALLPALFLLIQAIGASFGYKWNFVILNQQLAAVVNAAFALLAI
VGVVADPTTSGLGDSDRVLNKDKSEENK product="holin" (homology to Orf78 of phage HP1 and gene S of phage P21)
protein_id="AAC45168.1"
db_xref="GI:915370"
translation="MRFNMLKNSETTGAYVGSAIAIYSGFTLADWAAIFGILFGLFT M LINWYYKNK
EIKLKETALKQKIDLKEGDHE product="holin" (Bacillus phage GA-1)
function="host cell lysis, holin formation"
protein_id="CAC21535.1"
db_xref="GI:12141291"
translation="MFEFFHSLMETDDTKVYFLLGIIGVLNIVDFFFGFINAKFNKSIAYKSSKTIDGIMRKMKFTI
MAILFIPVSVLMPEPIGLGALYVFYFGYIYAELNSILSH LKLSEDGKETEVFLDFINTFFNSTKGDKKDD gene="hol187" (Staphylococcus phage 187)
function="forms pores to allow access of lysin to CW"
product="holin protein Hol187"
protein_id="CAA69023.1"
db_xref="GI:2764984"
translation="MLMVIMVGNVGIYLTIFLIDTGTLRHQATQEIWHGIDILKGLKC LETLLILSLNQVI gene="s" /function="holin" (Shigella dysenteriae)
product="S protein"
protein_id="CAC05628.1"
db_xref="GI:9955825"
translation="MYQMEKITTGVSYTTSAVGMGYWFLQFLDRVSPSQWAAIGVLGSLLFGLLTYLTNLYFKI
REDRRKAARGE gene="E"
protein_id="CAA42879.1"
db_xref="GI:14781"
db_xref="SWISS-PROT:P31280"
translation="MERWTLLDILAFLLLLSLLLPSLLIMFIPSMYKQHASLWKARSLAKTLSMASSARLTPLSSS
RTPCVLKQDSKKL gene="xhlB" (B.subtilis DNA (28 kb PBSX/skin element region)
product="holin-like protein"
protein_id="CAA94048.1"
db_xref="GI:1225964"
db_xref="SWISS-PROT:Q99163"
translation="MNTFDKGTVIRTVLLLIALINQTMLMLGKSPLDIQEEQVNQLADALYSAGSIAFTIGTTLAA
WFKNNYVTEKGKKQRDLLRDNNLTK

Fig. 3 gene="bhlA" (Bacillus subtilis 168 prophage)
product="holin-like protein"
protein_id="AAC38301.1"
db_xref="GI:2997596"
translation="MEMDITQYLSTQGPFAVLFCWLLFYVMKTSKERESKLYNQIDSQNEVLGKFSEKYDVVIE
KLDKIEQNFK gene="bhlB" (Bacillus subtilis 168 prophage)
product="holin-like protein"
protein_id="AAC38302.1"
db_xref="GI:2997597"
translation="MFENIDKGTIVRTLLLAIALLNQIMVMLGKAAFIINEEDINHLYDCLYTIFTIVFTTSTTTAA
WFKNNYITAKGKKQKQVLKKENLFK gene="hol" (Bacteriophage phi-Ea1h)
specific_host="Erwinia amylovora
function="pore formation"
product="holin"
protein_id="CAC17008.1"
db_xref="GI:11342496"
translation="MRKIYYVIITTIVVAGLIWAFIATQVNTGVTSKRQEDALAVSEANVGIGKEAKDQGEQATK
RADVAKEQRTHQINQLKDKLHEKAESYDSIPLSPSDVDILC RAYRSTDPVCSPTVKSD

Fig. 3

Alignments Lysis-Protein (Phagen)

product="lysis protein" (Phage phiX174)
function="host cell lysis"
protein_id="CAA84691.1"
translation="MVRWTLWDTLAFLLLLSLLLPSLLIMFIPSTFKRPVSSWKALNLRKTLLMASSVRLKPLNCS
RLPCVYAQETLTFLLTQKKTCVKNYVQKE

Fig. 3

* peptide nucleic acid transport complex

4 PNA$_{/Ampresistgene}$ (2.5 μM) - 10 μl
1μl E. Coli + 10 10 μl PNA
in LB medium

Test for NOI₁-Toxicity in eucaryotic cells (HeLa)
A
HeLa Control (untreated)
B
PNA*_KANRESGENE - 25 μM
PNA*_AMPRESGENE - 25 μM
Fig. 11

1

CONJUGATE FOR TREATING PROKARYOTIC INFECTIONS

CROSS-REFERENCE TO RELATED APPLCATIONS

This application is filed under the provisions of 35 U. S.C. §371 and claims the priority of International patent application No. PCT/DE03/00124 filed Jan. 17, 2003, which in turn claims priority of German patent application No. 102 01 862.6 filed on Jan. 18, 2002.

FIELD OF THE INVENTION

The present invention relates to a conjugate for treating prokaryotic infections from a transport mediator penetrating the prokaryotic cell membrane and a desired compound to be introduced into the prokaryote and directed thereagainst, which is preferably a peptide nucleic acid (PNA) directed against a prokaryote gene giving antibiotic resistance.

BACKGROUND OF THE INVENTION

Bacterial infections which on account of a resistance formation can no longer be treated with the currently available antibiotics are advancing worldwide. The situation is critical above all in clinics, e.g. in intensive-care units, where antibiotics are administered daily and pathogens can easily develop resistances. Also, the incorrect or excessive use of antibiotics has rapidly increased the number of resistant bacterial strains. Although the problem has previously been solved by using alternative or newly developed antibiotics (e.g. cephalosporins/derivatized antibiotics) and combination therapies (e.g. cotrimoxazole/sulfonamides), new resistances also occur in this case in a relatively short period of time. For example, vancomycin, which was active against certain bacterial strains a short time ago, often can no longer be used in therapy on account of the meanwhile formed resistances. Although major efforts are made to develop new natural antibiotics of different origin from prokaryotes and eukaryotes, only temporary or partial success has been achieved with respect to the rapidly mutating bacterial strains.

SUMMARY OF THE INVENTION

Thus, the invention is substantially based on the technical problem of providing means enabling an effective therapy of diseases correlated with prokaryotes, e.g. bacteria, resistant to antibiotics.

This technical problem is solved by providing the embodiments characterized in the claims.

In order to solve this technical problem, the inventors re-sensitized the bacteria with respect to the (classical or modern) antibiotics against which they were resistant. For this sensitization a conjugate was developed comprising the following components: (a) a transport mediator for the prokaryotic cell membrane, i.e. preferably a peptide (e.g. defensin) antibacterial per se, which can penetrate, and damage, the bacterial cell wall on account of its charge and structure by pore formation, and (b) the compound to be introduced into the prokaryote, e.g. a peptide nucleic acid (PNA) which is preferably directed against a gene giving the prokaryote an antibiotic resistance. By means of the examples resulting in the present invention it was possible to show that the antibiotic resistance of bacteria (*E. coli*) resistant to ampicillin/neomyin, which were treated with specific defensin-conjugate-PNAs$_{ampicillin/neomycin}$, has been overcome successfully.

Thus, the conjugates according to the invention are a new class of antibiotics which can overcome the bacterial defense mechanisms or by means of which it is possible to give back the original activity to already known classical antibiotics, such as benzylpenicillins, tetracyclines, and neomycins. This differs completely from the former therapy and research strategies, yet supplements them in a very promising way. The (dual) strategy which can be carried out by means of the present invention specifically addresses to prokaryotic, e.g. bacterial, membranes and is toxic to prokaryotes, on the one hand, and compounds directed against prokaryotes, e.g. antisense nucleic acids (anti-gene nucleic acids) directed specifically against bacterial genes, e.g. PNAs, peptide domains, modified nucleotides, inhibitors of enzymes, etc., can be introduced by means of the conjugates according to the invention, on the other hand.

The conjugates according to the invention thus have inter alia the following advantages: (a) no expensive screening method is required for establishing them, and (b) the revitalization of classical antibiotics can be achieved in a special embodiment by blocking the prokaryotic resistance mechanisms on the nucleic acid level so that the "old" antibiotics which were no longer usable in many cases on account of their lacking activity, regain significance.

Thus, the present invention relates to a conjugate suited fro treating prokaryotic infections and comprising the following components:

(a) a transport mediator passing through the prokaryotic cell membrane; and (b) a compound to be introduced into the prokaryote and directed thereagainst.

The term "compound to be introduced into the prokaryote and directed thereagainst" as used herein relates to any compound detrimental to the prokaryote, e.g. kills it or prevents the growth and/or division thereof. Suitable compounds are known to the person skilled in the art, they comprise e.g. anti-metabolites, modified nucleotides, etc.

As to methods of producing the individual conjugate components and their linkage, reference is made to German patent application No. 199 33 492.7 and the below examples. The other components (e.g. spacer and/or PNA) are linked to the transport mediator by a covalent chemical bond. Where appropriate, a redox cleavage site (—S∩S—) between transport mediator and compound to be introduced can be introduced chemically by means of a redox coupling. Also, a covalent bond, preferably an acid-amide bond, exists between an optionally present spacer and the compound to be introduced, e.g. the PNA. Possible alternatives are ether or ester bonds, depending on the functional group(s) present in the compound to be conjugated.

The conjugate according to the invention is suited for treating all prokaryotic infections, e.g. infections with bacteria, preferably human pathogen bacteria, mycoplasms or yeasts.

The transport mediator of the conjugate according to the invention is preferably a peptide or protein which can penetrate the prokaryotic cell membrane and can introduce the desired compound into the cytoplasm. The length of this peptide or protein is not subject to limitation as long as it has the above property. The selected transport mediator is preferably produced biologically (purification of natural transport mediator proteins/peptide or cloning and expression of the sequence in a eukaryotic or prokaryotic expression system) and in particular synthetically, e.g. according to the Merrifield method (Merrifield, J. Am. Chem. Soc. 85 (1963), 2149).

This transport mediator is preferably a compound which as such is already detrimental to the prokaryote, e.g. by damaging the membranes (e.g. by forming pores or lesions). These are preferably defensins or holins (bacteriophage protein domains).

In a particulary preferred embodiment, the conjugate according to the invention comprises a transport mediator which includes a phage-holin protein, a phage-holin protein with one of the amino acid sequences shown in Fig. 3 or fragments or variants thereof which can still penetrate the prokaryotic cell membrane, being even more preferred.

The terms "variant" and "fragment" used in the present invention comprise proteins/peptides having amino acid sequences which differ with respect to the sequences indicated in FIG. 3 by deletion(s), insertion(s), substitution(s) of amino acid residues and/or other modifications known in the art or comprise a fragment of the original protein/peptide, the variants and/or fragments of the protein/peptide substantially having maintained the biological properties of the initial protein/peptide, i.e. may penetrate the prokaryotic cell membrane. Methods of producing the above modifications in the amino acid sequence are known to the person skilled in the art and described in standard works of molecular biology, e.g. in Sambrook et al., Molecular Cloning: A Laboratory Manual, $2^{nd}$ edition, Cold Spring Harbor Laboratory Press, Cold Spring Harbor N.Y. (1989)). The person skilled in the art can also determine whether such a protein or peptide still has the desired biological properties, e.g. by the methods described in the below examples.

In another alternative preferred embodiment of the conjugate according to the invention, the transport mediator comprises a defensin, preferably a human defensin. The defensins are polypeptides or peptides having an antimicrobial activity, which represent important factors in the innate immunity of vertebrates and non-vertebrates. Defensins have been isolated from animals (including humans), plants and insects, for example. They usually consist of 29 to 42 amino acids and contain three disulfide bridges formed of three cysteine pairs. Defensins suited for the present invention are described in Tang et al., Science 286 (1999), 498; Saido-Sakanaka et al., Biochem. J. 338 (1999), 29; Raj et al., Biochem J. 347 (2000), 633; Yu et al., J. Biol. Chem. 275 (No. 6) (2000), 3943, for example.

In an even more preferred embodiment of the conjugate according to the invention, the compound to be introduced into the prokaryote is a peptide nucleic acid (PNA) directed against the expression of a gene. On account of their physicochemical properties, the use of the protease and nuclease-resistant peptide nucleic acids ("PNAs") which are oligonucleotide derivatives where the sugar phosphate backbone is preferably substituted by ethyl-amine-bound α-amino-ethyl-glycine units, permits a stable and efficient blocking of the transcription of the desired genes under physiological conditions. An anti-gene strategy based on the antisense-principle is pursued by using these PNAs, where it is not the mRNA but the gene per se that is the target. Here, the PNAs hybridize to the target DNA by forming a triple helix. The target area can be a transcribed region of the gene to be blocked, e.g. of the gene giving antibiotic resistance, on the one hand, or a regulatory region whose blocking by means of PNAs also inhibits the transcription, on the other hand. Suitable regions can be identified by the person skilled in the art by means of the known DNA sequences or the function thereof. The peptide nucleic acids preferably have a length of at least 15 base pairs, peptide-nucleic acids having a length of at least 18 bases are particularly preferred, and of at least 21 bases are even more preferred and of at least 23 base pairs are most preferred. The peptide nucleic acid can optionally be labeled, e.g. radioactively, using a dye, biotin/avidine etc. The synthesis of PNAs is known to the person skilled in the art and also described in Nielsen et al., Science 254 (1991), 1497-1500, for example. The term "gene" used herein does not only comprise genes of the prokaryote genome but also genes on extra-genomic elements, e.g. plasmids, etc.

In an even more preferred embodiment of the conjugate according to the invention, the peptide-nucleic acid (PNA) is directed against a gene which gives an antibiotic resistance, preferably the antibiotic resistance is a resistance to penicillin, ampicillin, kanamycin or tetracycline.

Furthermore, the conjugate may optionally contain a spacer which is located between the transport mediator and the compound to be transported, e.g. the peptide-nucleic acid (PNA). The spacer serves for eliminating or favorably influencing optionally existing steric interactions between the components.

The structure of the conjugate according to the invention is preferably as follows: transport mediator-spacer-compound to be introduced. The spacers polylysine, polyglycine or poly (glycine/lysine) are particularly preferred. The length of the spacer is preferably within a range of 2 to 6 amino acids for the purposes according to the invention. The spacer is preferably linked with the transport mediator by means of a cleavable disulfide bridge (—S∩S—).

In a particularly preferred embodiment of the conjugate according to the invention, the peptide-nucleic acid (PNA) comprises the following sequence: ATTGTTAGATTTCAT (SEQ ID NO: 1) (orientation: N-terminus/sequence/C-terminus).

The present invention finally also relates to a medicament comprising a conjugate according to the invention, optionally together with a suitable carrier. The medicament preferably comprises an antibiotic for which the prokaryote was sensitized by administering the conjugate. Suitable carriers and the formulation of such medicaments are known to the person skilled in the art. Suitable carriers are e.g. phosphate-buffered common salt solutions, water, emulsions, e.g. oil/water emulsions, wetting agents, sterile solutions, etc. The medicaments are preferably administered parenterally, transdermally or subcutaneously. The suitable dosage is determined by the attending physician and depends on various factors, e.g. on the patient' age, sex and weight, the kind and stage of the infection, the kind of administration, etc.

Finally, the present invention relates to the use of a conjugate according to the invention for treating a prokaryotic infection, this infection being preferably caused by a prokaryote which is resistant to an antibiotic.

Legends of the figures:

FIG. 1: Diagram of a conjugate according to the invention using defensin as a transport mediator and a PNA directed against a resistance to ampicillin or kanamycin FIG. 2: Presentation of a pDNA segment of plasmid pBR322 including the sequences used for the design of a PNA conjugate The sequence (SEQ ID NO: 3)of the anti-gene PNA directed against an ampicillin resistance is shown in the figure below. The underlined region of the beta-lactamase-encoding pDNA sequence of pBR322 corresponds to the target region for the PNA conjugate.

FIG. 3: List of Holin-protein sequences which are suited as a transport mediator in the conjugates according to the invention The amino acid sequences (SEQ ID NOs: 4-31) of the 28 individual holins are shown in the one-letter code. FIG. 3(1) shows SEQ ID NO: 24-31, FIG. 3(2) shows SEQ ID NOs: 4-11, FIG. 3(3) shows SEQ ID NOs: 11-19, FIG. 3(4) shows SEQ ID NOs: 20-22, and FIG.3(5) shows SEQ ID NO: 23.

FIG. 4: Results of treating the competent *E. coli* resistant to ampicillin by transformation with pBR322 and/or to kanamycin by transformation with pEGFP-N$_1$ (Clontech, Germany, Heidelberg) with or without (control) the conjugates according to the invention Top row: kanamycin culture medium+kanamycin resistance conjugate (500 nM); bottom row: ampicillin agar+ampicillin resistance conjugate (500 nM); left column: controls (without PNA conjugates). A clear effect of the conjugates according to the invention (regaining the antibiotic sensitivity) can be observed.

Figure 5:
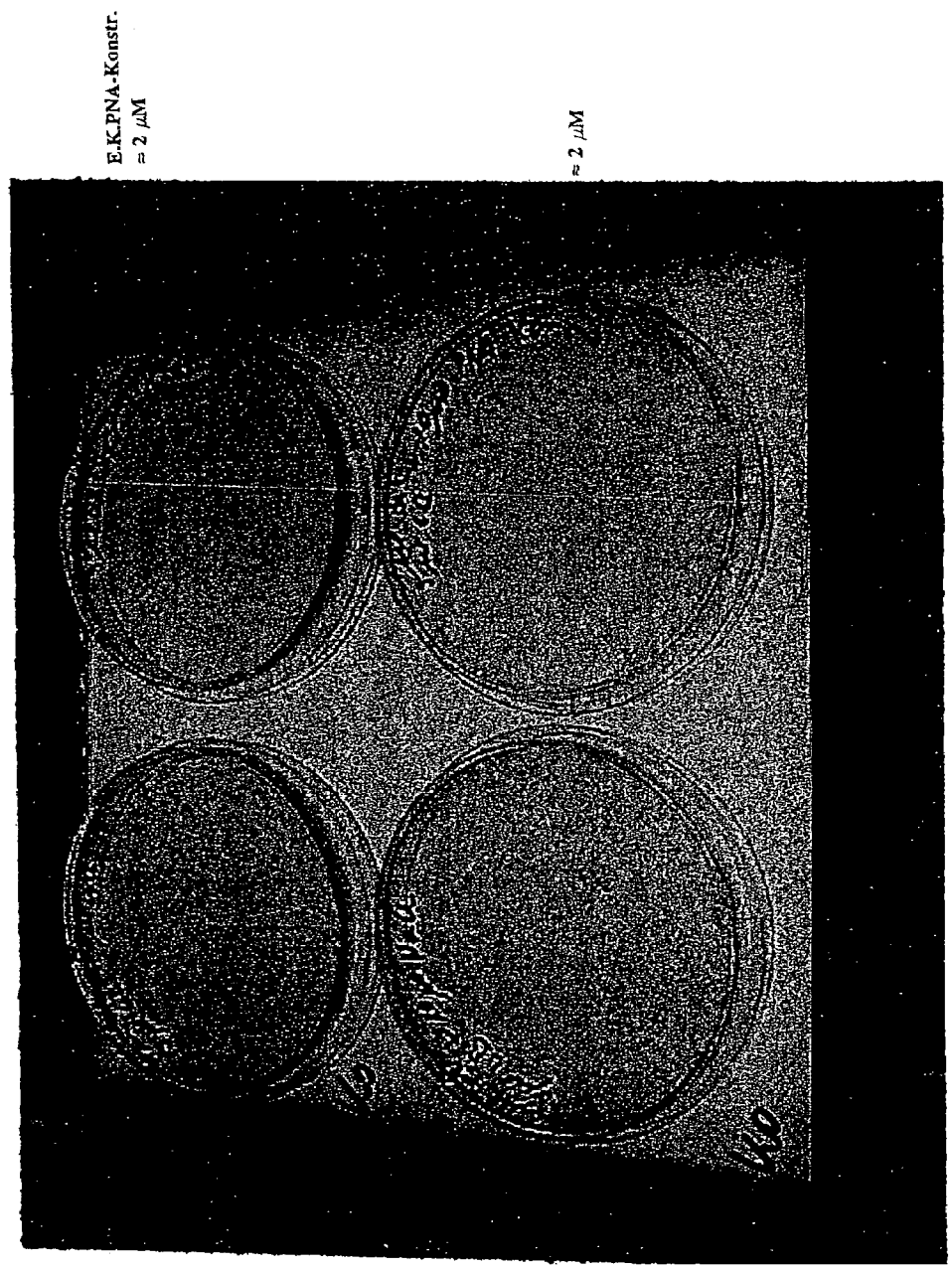

FIG. 5: Results of the treatment of intact (non-competent) *E. coli* resistant to kanamycin with or without (control) the conjugates according to the invention Top row: kanamycin culture medium+kanamycin resistance conjugate (2 µM); bottom row: kanamycin culture medium+kanamycin resistance conjugate (20 µM); left columns: controls (without PNA conjugates). A clear effect of the conjugates according to the invention (regaining the antibiotic sensitivity) can already be observed at a concentration of 2 µM. All of the bacteria are again sensitized, i.e. killed, at 20 µM.

Figure 6:
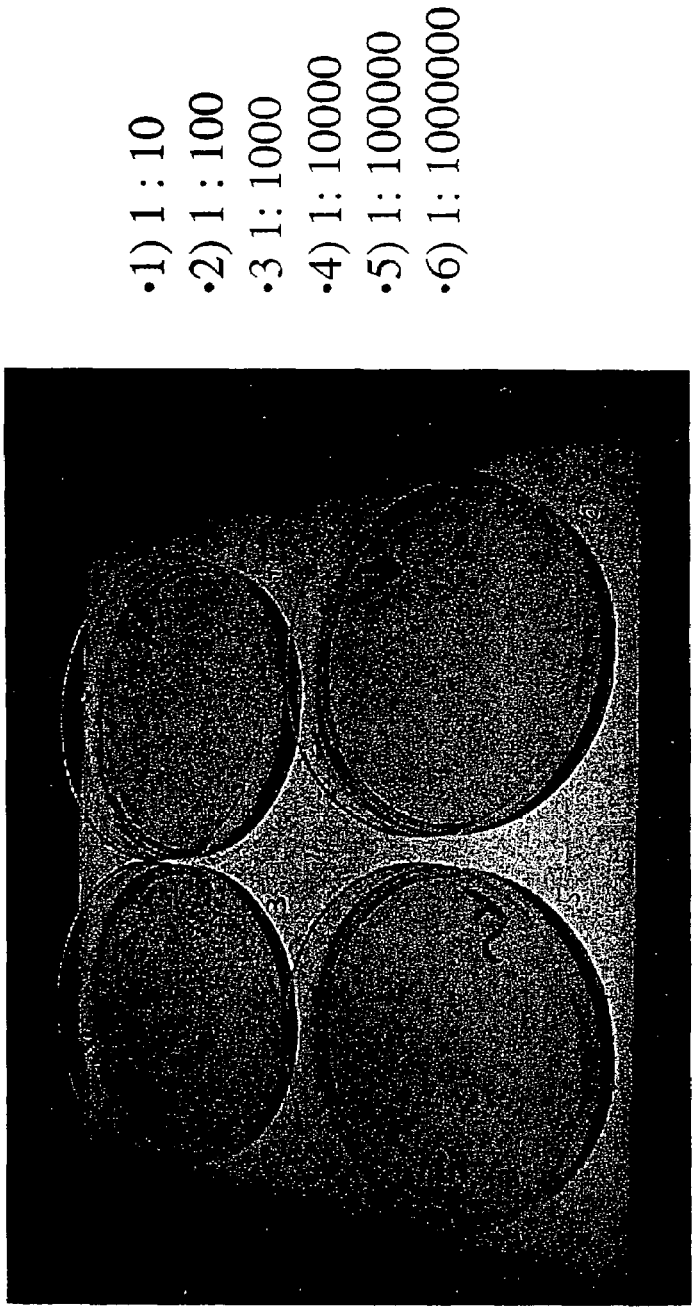

FIG. 6: Results of the treatment of intact (non-competent) *E. coli* resistant to kanamycin at different concentrations of the conjugates according to the invention to determine the optimum bacterial concentration for the purpose quantification Kanamycin culture mediums were used onto which resistant bacteria were plated. In order to determine the optimum bacterial concentration, a dilution series having the kanamycin resistance conjugate were used with decreasing decimal powers.

Figure 7:
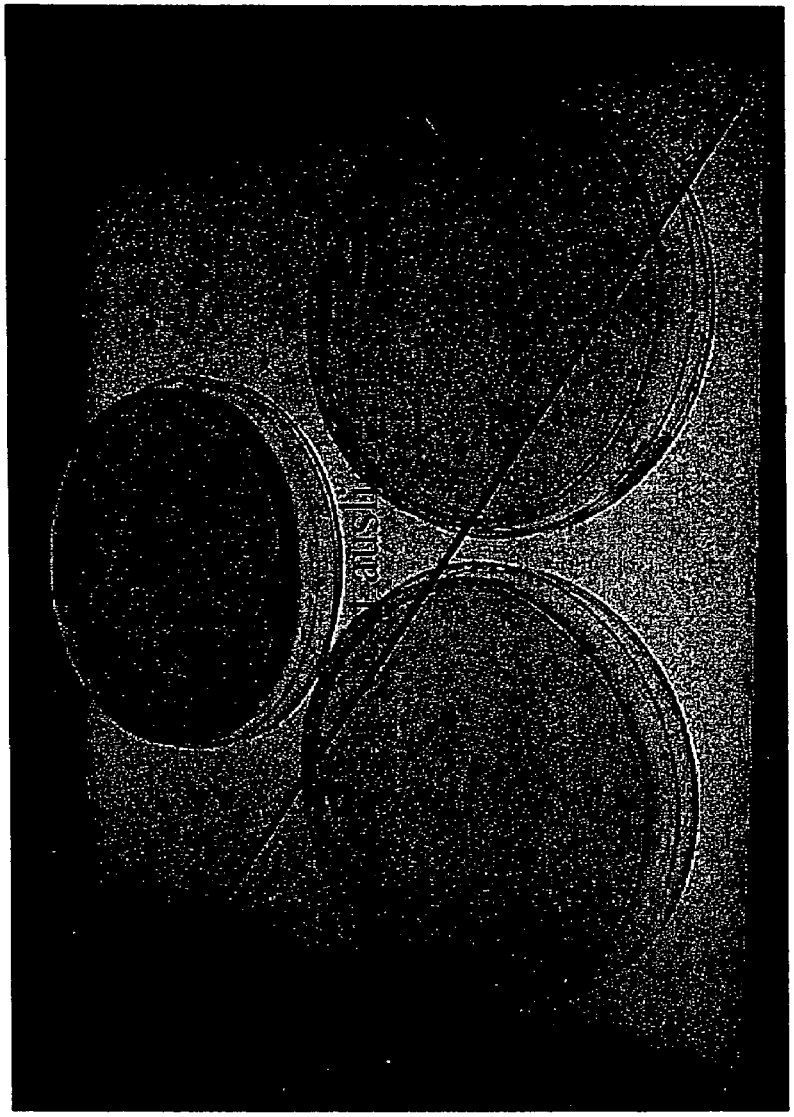

FIG. 7: Results of treating intact (non-competent) *E. coli* resistant to kanamycin or ampicillin with the conjugates according to the invention Plate K1: control, plate 2: 250 nM kanamycin-resistance conjugate; plate 3: 250 nM ampicillin resistance conjugate. The results show a bacterial inhibition for ampicillin and kanamycin with 250 nM conjugate.

Figure 8:
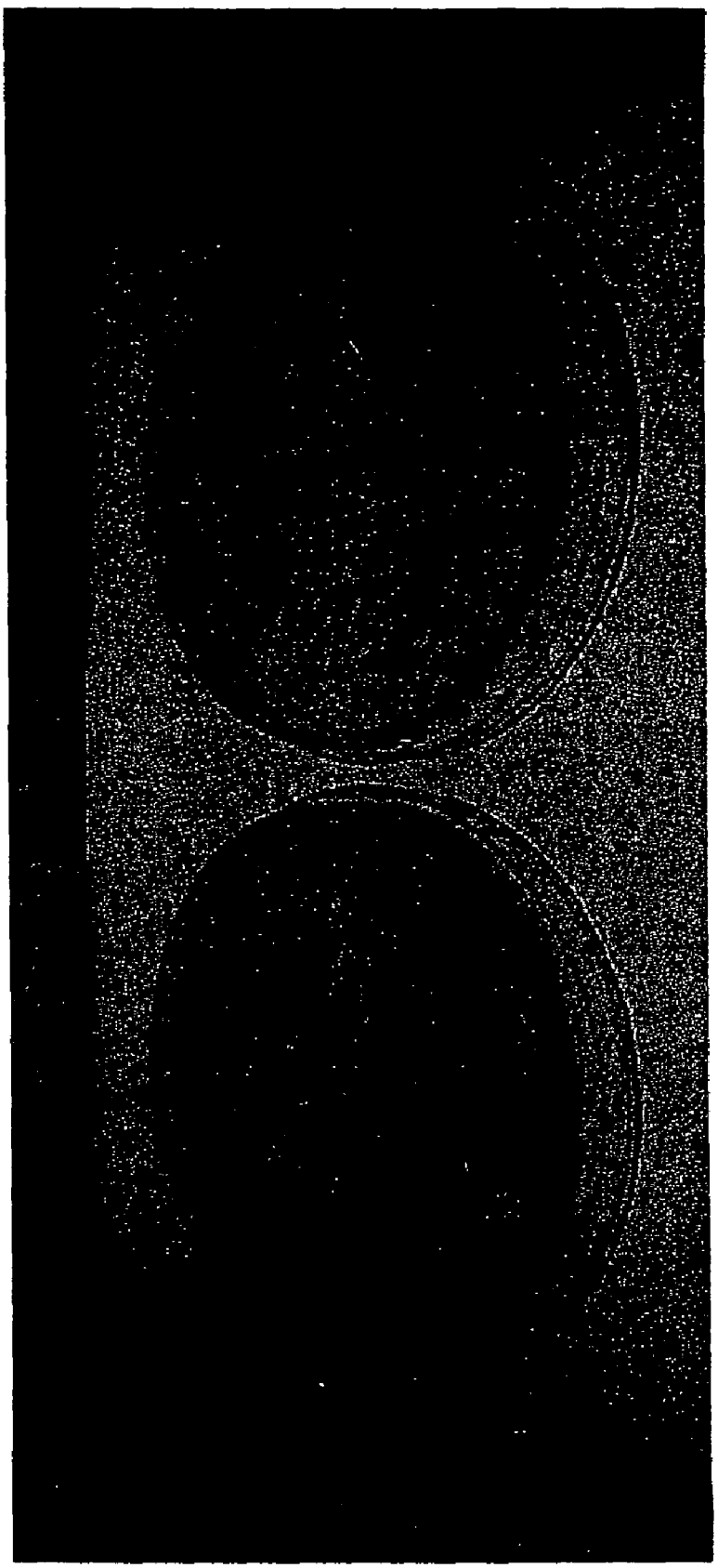
Figure 9:
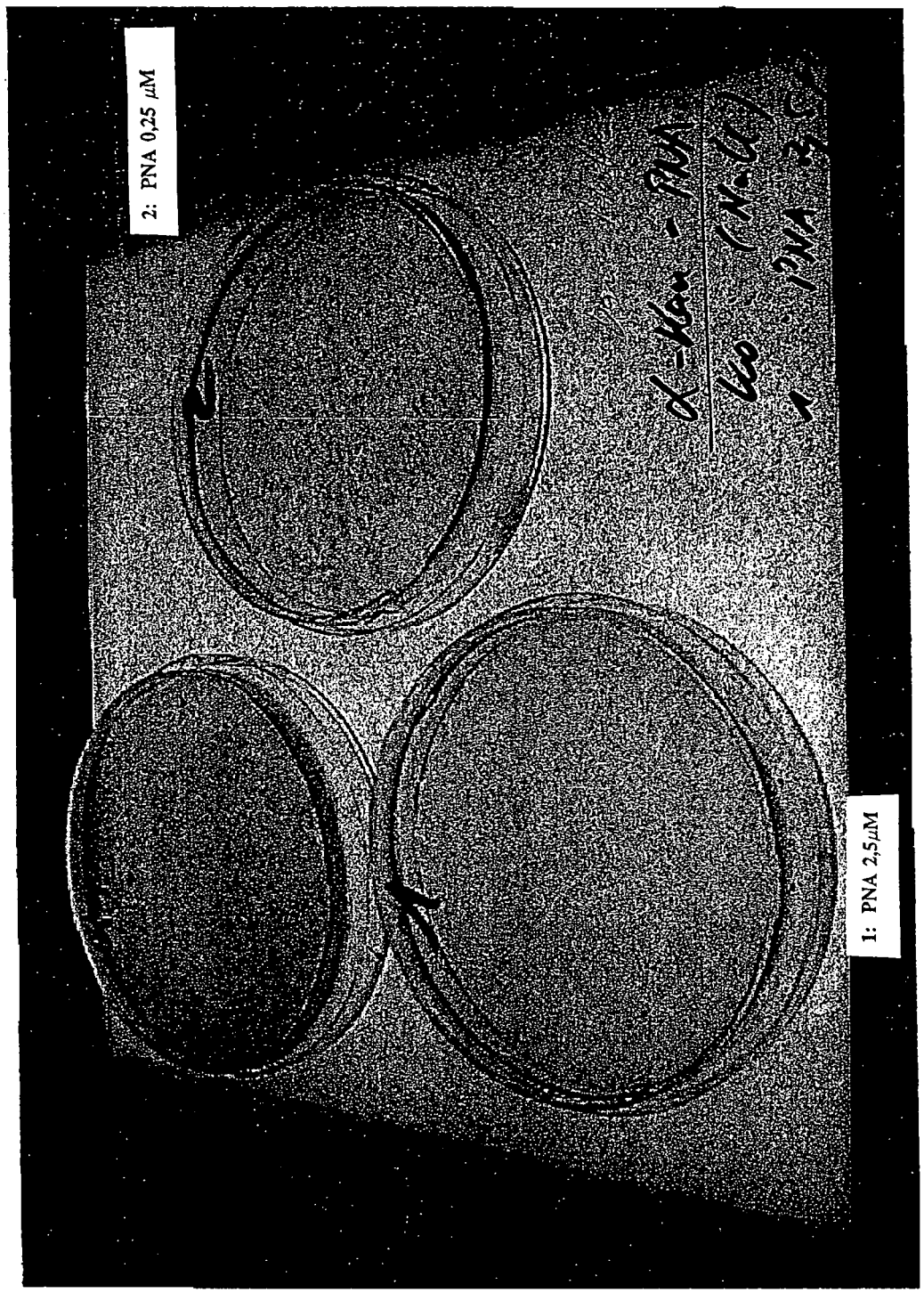

FIG. 8: Results of treating intact (non-competent) *E. coli* resistant to ampicillin with the conjugates according to the invention as in FIG. 7; K2: control, plate 4: 250 nM ampicillin resistance conjugate FIG. 9: Results of treating intact (non-competent) *E. coli* resistant to kanamycin with the conjugates according to the invention as in FIG. 6; K1: control; plate 1: 2.5 µM kanamycin resistance conjugate; plate 2: 250 nM kanamycin resistance conjugate.

Figure 10:
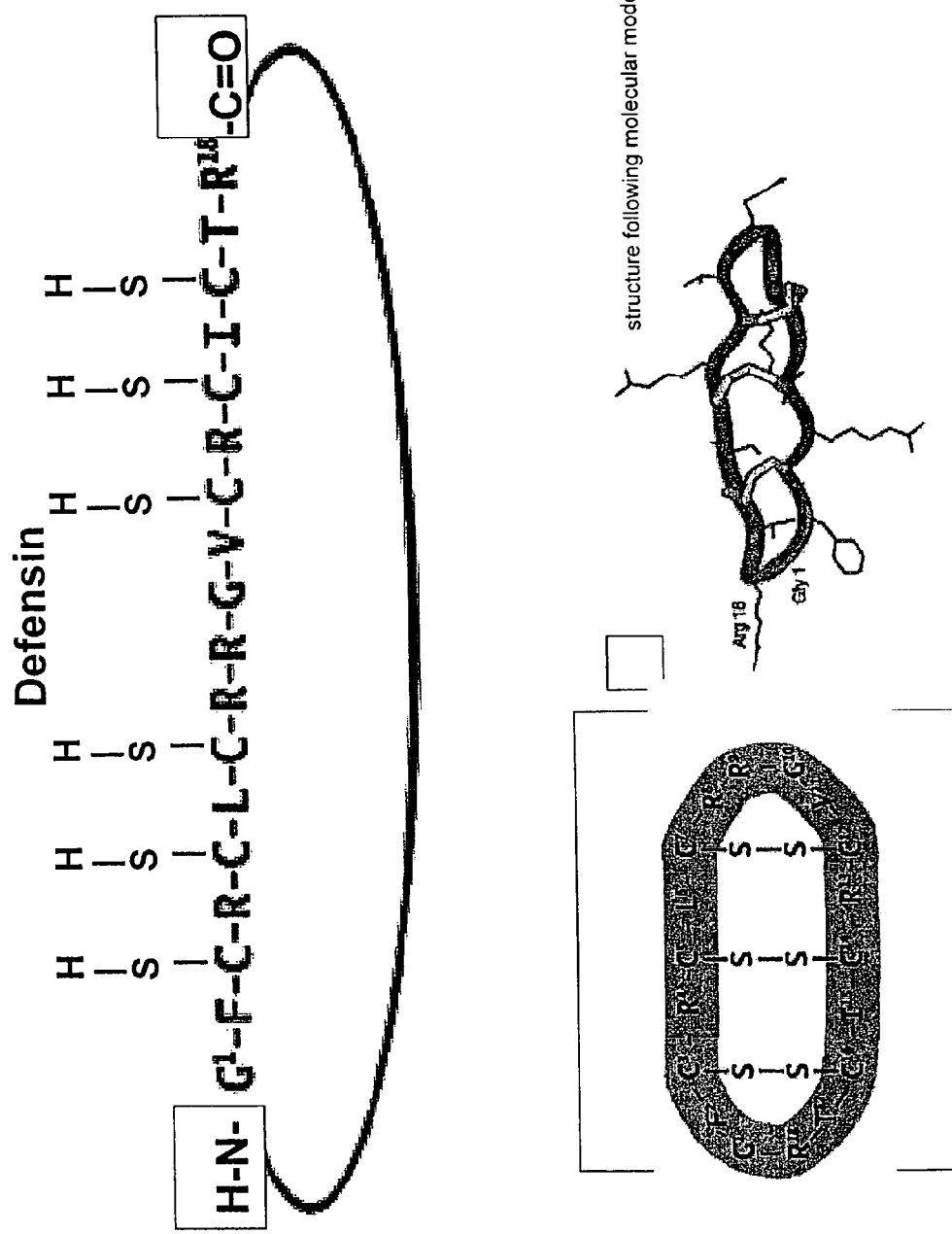

FIG. 10: Structure of defensin used for the conjugates according to the invention following cyclization (top) and following the formation of three disulfide bridges (left bottom)

The hypothetical spatial conformation is shown on the right bottom.

FIG. 11: Results of treating HeLa cells with a conjugate according to the invention A: untreated control B: cells treated with the conjugate according to the invention The invention is further described by means of the below examples.

DETAILED DESCRIPTION OF THE INVENTION

EXAMPLE 1

General Methods (A) Cell Culture

The bacteria were plated onto agar with LB broth (and the corresponding antibiotics) and incubated at 37° C. overnight. HeLa cells were cultured in a liquid culture under common conditions.

(B) PNA Synthesis

Peptide nucleic acid (PNA) imitates a DNA and was originally developed as a reagent for the sequence-specific recognition of double-stranded DNA via a conventional triple helix formation. For the solid phase synthesis the Fmoc strategy was used by means of a fully automated synthesis device (Syro II, Multisyntech, Witten, Germany). The synthesis was carried out on a 0.05 mmol Fmoc-AS polystyrene resin (1% cross-linked). The coupling reagent used was 2-(1H-benzotriazole-1-yl)-1,1,3,3-tetramethyluroniumhexafluorophosphate (HBTU). The side chain-protecting groups were Lys(Boc), Asp(OBut), Ser(But), Cys(Trt) and Asn(Trt). The protected peptidyl resin was treated with 20% piperidine in dimethylformamide. The cleavage and separation of the protecting groups were obtained by treatment with 90% trifluoroacetic acid, 5% ethane dithiol, 2.5% thioanisole and 2.5% phenol (v/v/v) at room temperature for 2.5 hours. All of the products were precipitated in ether and purified by preparative HPLC (Shimazu LC-8A, Shimazu, Duisburg, Germany) on a YMC ODS-A 7A S-7 µm reverse phase HPLC column (20×250 mm) using 0.1% trifluoroacetic acid in water (A) and 60% acetonitrile in water (B) as an eluting agent. The peptides were eluted with a linear gradient of 25% B to 60% B at a flow rate of 10 ml/min within 40 minutes. The fractions corresponding to the purified conjugate were lyophilized. Sequences of individual molecules and the complete bimodular construct were characterized by analytical HPLC (Shimadzu LC-10) and laser desorption mass spectroscopy (Finnigan Vision 2000, Finnigan MAT, San Jose, Calif., U.S.A.) as described below.

The sequence of the PNA directed against an ampicillin resistance was as follows: H$_2$N -ATTGTTAGATTTCAT-COOH (SEQ ID NO: 1). This is a sequence which can hybridize with the region of position 86 to position 100 of the pDNA of pBR322 (GeneBank accession number J01749). The sequence of the PNA used against the kanamycin resistance was H$_2$N -TCTTGTTCAATCAT-COOH (SEQ ID NO: 2).

(C) Chemical Synthesis of Defensin

For the solid phase synthesis of defensin (cf. FIG. 10 as regards the amino acid sequence and structure) the Fmoc strategy (Merrifield, J. Amer. Chem. Soc. 85 (1963), 2149-2154; Ruegg and Rudinger, Methods Enzymol. 47 (1977), 111-126) was used with a fully automated synthesis device (ABI 431; Applied Biosystems, Germany, Darmstadt). The synthesis was carried out on a 0.05 mmol Fmoc-Arg(Pbf) polystyrene resin (1% cross-linked). 2-(1H-benzotriazole-1-yl)-1,1,3,3-tetramethyluroniumhexafluorophosphate (HBTU) was used as the coupling reagent. The side chain-protecting groups were: Thr(But), Arg(Pbf). Three different selectively cleavable protecting groups were used for Cys.

t-Butylthio was used for Cys(3,15), acetamidomethyl was used for Cys(5,13) and a trityl group was employed for Cys (7,11).

In the first step, the t-butylthio protecting group was cleaved using tris(2-carboxyethyl)phosphine (TCEP) and the sulfur bridge was cleaved with 20% DMSO in water. In the second step, the acetamidomethyl. protecting group was cleaved and at the same time, the second sulfur bridge was oxidized with a 0.01 mole iodine solution. The protected peptidyl resin was treated with 20% piperidine in formamide for 12 min. and then thoroughly washed with dimethylformamide. The protecting groups were cleaved and removed from the peptide resin by treatment with 90% trifluoroacetic acid, 5% ethane dithiol, 2.5% thioisanole and 2.5% phenol (v/v/v/v) at room temperature for 2.5 hours. The product was precipitated in ether. The raw material was purified on preparative HPLC (Shimazu LC-8A, Shimazu, Duisburg, Germany) on a YMC-Pack ODS-A,S-5 µm reverse phase HPLC column (20×150 mm) using 0.1% trifluoroacetic acid in water (A) and 60% acetonitrile in water (B) as an eluting agent. The peptide was eluted with a linear gradient of 25% B to 60% B at a flow rate of 20 ml/min for 40 min. The fractions corresponding to the purified peptide were lyophilized.

As the last step, a head/tail/cyclization was carried out with propane phosphonic acid anhydride (T3P), and the purification method was repeated. The purified material was characterized by analytical HPLC (Shimadzu LC-10) and laser desorption mass spectroscopy (Finnigan Vision 2000, Finnigan MAT, San Jose, Calif., U.S.A.).

Peptide Purification:
Gradient: analytical 5%→80% (in a period of 35 min.); preparative: 5%→80% (in a period of 40 min.);
Purity: >90%.

(B) Linkage Reactions

The linkage reactions were effected as described in German patent application no. 199 33 492.7 under mild oxidative conditions (DMSO/H$_2$O). For this purpose, cysteine groups of defensin and the spacer H—S-Gly and the PNA were oxidized in a region of 2 mg/ml in a 20% DMSO/water solution. The reaction was complete after about 5 hours. The course of the oxidation was monitored by analytical C18 reverse phase HPLC (Tam et al., J. Amer. Chem. Soc. 113 (1991)). The components were linked according to the Merrifield method (Merrifield, J. Americ. Chem. Soc. 85 (1963), 2149).

The thus synthesized PNA module has the following structure:

DEFENSIN$_{human}$-S∩S-(Gly)X-PNA$_{AmpR/NeoR}$

X=1-5

The purification was made by means of reverse phase HPLC, following by lyophilization. Having determined the mass by means of MS, the lyophilizate was dissolved in a defined volume of physiological common salt solution to give a stock solution of 10 µM.

EXAMPLE 2

Determining the Activity of the Conjugates According to the Invention in the Case of Antibiotic-Resistant E. coli Strains Resistant bacteria were confluently plated onto common agar plates with and without antibiotic and partially treated with the conjugates according to the invention. In a preliminary experiment, already competent E. coli (i.e. having already perforated membranes) were used; see FIG. 4; top row: kanamycin culture medium+kanamycin resistance conjugate (500 nM); bottom row: ampicillin agar+ampicillin resistance conjugate (500 nM); left columns: controls. A marked effect of the conjugates according to the invention (regaining the antibiotic sensitivity) can be observed.

In the then following experiments (shown in FIGS. 5 to 9), intact (non-competent) E. coli were used, and the conjugates directed against an antibiotic resistance were tested at various dilutions. As to the employed bacteria, antibiotics and concentrations, reference is made to the legend of the figures. In any case, the results of these studies clearly show that the conjugates according to the invention effect another sensitization of the bacterium for the corresponding antibiotic by means of a PNA directed against a gene giving antibiotic resistance and that they can thus be combated by means of this antibiotic again.

The non-toxic effect of this conjugate on eukaryotic cells (HeLa cells) was detected by incubation of the cells with/without conjugate (at concentrations as for the experiments with bacteria); see FIGS. 11A+11B.

The invention claimed is:

1. A conjugate suited for treating prokaryotic infections, comprising the following components:
   (a) a phage-holin protein as transport peptide or protein adapted to penetrate the infectious prokaryote; and linked by a covalent bond thereto;
   (b) a peptide nucleic acid (PNA) to be introduced into the prokaryote and directed against a DNA of a gene giving antibiotic resistance, wherein the peptide nucleic acid inhibits the transcription of the gene.

2. The conjugate according to claim 1, wherein the prokaryote is a bacterium pathogenic for humans.

3. The conjugate according to claim 1 wherein the phage-holin protein comprises one of the amino acid sequences of SEQ ID NOs: 4 to 31.

4. The conjugate according to claim 1 wherein the antibiotic resistance is a resistance to penicillin, ampicillin, kanamycin or tetracycline 5. The conjugate according to claim 1 which has the following structure: phage-holin protein-spacer -(PNA-)-

6. The conjugate or conjugate mixture according to claim 5, wherein the spacer is polylysine, polyglycine or poly(glycine/lysine).

7. The conjugate according to claim 5,wherein the spacer is linked to the phage-holin protein via a cleavable disulfide bridge.

8. The conjugate according to claim 1, wherein the PNA comprises the sequence $H_2$N-ATTGTTAGATTTCAT-COOH (SEQ ID NO: 1).

9. A medicament comprising the conjugate according to claim 1.

10. The medicament according to claim 9 further comprising at least one antibiotic for which the prokaryote was re-sensitized by administering the conjugate.

11. A conjugate suited for treating prokaryotic infections, comprising the following components:
   (a) a peptide selected from the group consisting of SEQ ID NOs: 4 to 31; and linked by a covalent bond thereto;
   (b) a peptide nucleic acid (PNA) to be introduced into the infectious prokaryote and directed against a gene giving antibiotic resistance.

* * * * *

SEQUENCE LISTING

<160> NUMBER OF SEQ ID NOS: 31

<210> SEQ ID NO 1
<211> LENGTH: 15
<212> TYPE: DNA
<213> ORGANISM: Artificial Sequence
<220> FEATURE:
<223> OTHER INFORMATION: Synthetic Construct

<400> SEQUENCE: 1
attgttagat ttcat                                     15

<210> SEQ ID NO 2
<211> LENGTH: 14
<212> TYPE: DNA
<213> ORGANISM: Artificial Sequence
<220> FEATURE:

<223> OTHER INFORMATION: Synthetic Construct

<400> SEQUENCE: 2
tcttgttcaa tcat                                                            14

<210> SEQ ID NO 3
<211> LENGTH: 600
<212> TYPE: DNA
<213> ORGANISM: Artificial Sequence
<220> FEATURE:
<223> OTHER INFORMATION: Synthetic Construct

<400> SEQUENCE: 3
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacaccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg caggccccg tggccggggg    540
actgttgggc gccatctcct tgcatgcacc attccttgcg gcggcggtgc tcaacggcct    600

<210> SEQ ID NO 4
<211> LENGTH: 109
<212> TYPE: PRT
<213> ORGANISM: Bacteriophage P1

<400> SEQUENCE: 4

Met Leu Asp Thr Gln Glu Leu Ala Pro Val Ala Ile Ala Leu Leu Leu
1               5                   10                  15

Ser Val Ile Gly Gly Ile Gly Thr Phe Leu Met Asp Val Arg Asp Gly
            20                  25                  30

Arg Gln Ser Gly Asn Leu Leu Gly Leu Val Thr Glu Ile Phe Val Ala
        35                  40                  45

Val Thr Ala Gly Ala Val Ala Tyr Leu Leu Gly Gln His Glu Gly Trp
    50                  55                  60

Glu Leu Ser Ile Thr Tyr Leu Met Val Thr Ile Ala Ser Asn Asn Gly
65                  70                  75                  80

His Glu Val Ile Ser Gly Met Lys Arg Val Asn Ile Asp Ser Ile Leu
                85                  90                  95

Asn Val Leu Thr Ser Leu Val Lys Lys Gly Gly Gly Lys
            100                 105

<210> SEQ ID NO 5
<211> LENGTH: 68
<212> TYPE: PRT
<213> ORGANISM: Bacteriophage H19B

<400> SEQUENCE: 5

Met Glu Lys Ile Thr Thr Gly Val Ser Tyr Thr Thr Ser Ala Val Gly
1               5                   10                  15

Thr Gly Tyr Trp Leu Leu Gln Leu Leu Asp Lys Val Ser Pro Ser Gln
            20                  25                  30

Trp Val Ala Ile Gly Val Leu Gly Ser Leu Leu Phe Gly Leu Leu Thr
            35                  40                  45

Tyr Leu Thr Asn Leu Tyr Phe Lys Ile Arg Glu Asp Arg Arg Lys Ala
    50                  55                  60

Val Arg Gly Glu
65

<210> SEQ ID NO 6
<211> LENGTH: 96
<212> TYPE: PRT
<213> ORGANISM: Bacteriophage A118

<400> SEQUENCE: 6

Met Ile Glu Met Glu Phe Gly Lys Glu Leu Leu Val Tyr Met Thr Phe
1               5                   10                  15

Leu Val Val Thr Pro Val Phe Val Gln Ala Ile Lys Lys Thr Glu
            20                  25                  30

Leu Val Pro Ser Lys Trp Leu Pro Thr Val Ser Ile Leu Ile Gly Ala
        35                  40                  45

Ile Leu Gly Ala Leu Ala Thr Phe Leu Asp Gly Ser Gly Ser Leu Ala
    50                  55                  60

Thr Met Ile Trp Ala Gly Ala Leu Ala Gly Ala Gly Gly Thr Gly Leu
65                  70                  75                  80

Phe Glu Gln Phe Thr Asn Arg Ser Lys Lys Tyr Gly Glu Asp Asp Lys
                85                  90                  95

<210> SEQ ID NO 7
<211> LENGTH: 143
<212> TYPE: PRT
<213> ORGANISM: Lactobacillus casei bacteriophage A2

<400> SEQUENCE: 7

Met Lys Ile Asn Trp Lys Val Ala Val Leu Ser Val Lys Phe Trp Leu
1               5                   10                  15

Ala Leu Val Pro Ala Ala Leu Leu Val Val Gln Thr Ala Ala Ala Val
            20                  25                  30

Phe Gly Tyr Asn Trp Asp Phe Ala Asn Leu Gly Lys Glu Leu Thr Ala
        35                  40                  45

Val Ile Asn Ala Val Phe Ala Leu Leu Thr Ile Val Gly Val Ala Val
    50                  55                  60

Asp Pro Thr Thr Glu Gly Val Ser Asp Ser Gln Gln Ala Leu Ala Tyr
65                  70                  75                  80

Pro Ala Leu Ile Thr Thr Lys Ala Ala Lys Ile Lys Ser Leu Glu Asp
                85                  90                  95

Gln Ile Lys Ala Leu Gln Ala Asp Lys Ala Ala Asp Gln Ala Thr Ser
            100                 105                 110

Ala Ala Ser Glu Val Val Pro Glu Thr Ser Ser Ala Ala Pro Ala Glu
        115                 120                 125

Ser Ala Pro Glu Ser Val Ala Pro Val Ala Ser Glu Glu Val Lys
    130                 135                 140

<210> SEQ ID NO 8
<211> LENGTH: 142
<212> TYPE: PRT
<213> ORGANISM: Lactobacillus bacteriophage phig 1e

<400> SEQUENCE: 8

Met Asp Ile Ile Thr Ser Leu Asn Leu Ala Thr Ala Gly Glu Leu Ala

```
               1               5                  10                 15
Leu Ile Ser Phe Phe Ile Gly Val Ile Val Gln Ala Ile Lys Lys Thr
                20                 25                 30

Gly Lys Val Lys Asn Thr Tyr Leu Pro Phe Ile Ser Met Gly Ile Gly
                35                 40                 45

Ile Leu Ala Gly Leu Ala Ala Val Val Thr Lys Asp Thr Asn Tyr
        50                 55                 60

Leu Asn Gly Ala Val Ala Gly Leu Ile Val Gly Ala Ala Thr Ser Gly
 65                 70                 75                 80

Leu Thr Asp Gly Leu Ser Val Gly Thr Ser Ala Val Thr Thr Ala Lys
                85                 90                 95

Ala Thr Lys Asp Ala Ala Lys Thr Ala Ala Ile Thr Gln Ala Val Leu
               100                105                110

Asn Ser Ile Asn Thr Thr Lys Ser Ser Asp Thr Thr Gln Val Ala Asn
        115                120                125

Thr Ser Asn Thr Glu Gly Gly Ser Thr Ser Glu Thr Gln Lys
130                135                140

<210> SEQ ID NO 9
<211> LENGTH: 107
<212> TYPE: PRT
<213> ORGANISM: Lactobacillus delbrueckii subsp. lactis bacteriophage
      LL-H

<400> SEQUENCE: 9

Met Thr Leu Ile Asp Trp Phe Asn Leu Ile Val Ala Ile Gly Thr Ile
 1               5                 10                 15

Ala Leu Ala Val Val Ala Ser Val Tyr Val His Leu Lys Ala Lys Ile
                20                 25                 30

Asp Thr Lys Thr Ala Ala Gly Lys Ala Phe Asp Leu Val Gly Lys Leu
                35                 40                 45

Ala Val Trp Ala Val Asn Glu Ala Glu His Ser Gln Asp Gly Gly Ala
        50                 55                 60

Ala Lys Arg Glu Phe Ala Ala Lys Leu Ile Ser Asp Gln Leu Lys Ala
 65                 70                 75                 80

Lys Gly Ile Thr Gly Ile Asp Glu Lys Met Val Tyr Gly Ala Val Glu
                85                 90                 95

Thr Ala Trp Lys Glu Ala Ile Glu Asn Val Lys
               100                105

<210> SEQ ID NO 10
<211> LENGTH: 44
<212> TYPE: PRT
<213> ORGANISM: Lactococcus phage c2

<400> SEQUENCE: 10

Met Ile Glu Thr Leu Arg Ala Ile Gly Leu Val Val Phe Met Gln Leu
 1               5                 10                 15

Leu Ser Leu Ala Leu Glu Phe Ile Asp Thr Gly Thr Leu Lys Pro Ser
                20                 25                 30

Val Arg Lys Arg Ile Ala Val Glu Leu Met Val Leu
                35                 40

<210> SEQ ID NO 11
<211> LENGTH: 74
<212> TYPE: PRT
<213> ORGANISM: bacteriophage phi AM2
```

<400> SEQUENCE: 11

Met Phe Phe Asn Asn Lys Phe Tyr Asn Val Ile Lys Trp Ala Val Leu
1               5                   10                  15

Thr Ala Leu Pro Ala Leu Ser Val Phe Ile Gly Val Ile Gly Lys Ala
            20                  25                  30

Tyr Gly Trp Gly Gly Thr Asp Leu Ala Ile Ile Thr Leu Asn Ala Phe
        35                  40                  45

Thr Val Phe Leu Gly Thr Leu Ala Gly Val Ser Ala Val Lys Tyr Asn
    50                  55                  60

Ser Gln Pro Asn Asp Thr Lys Glu Asn Lys
65                  70

<210> SEQ ID NO 12
<211> LENGTH: 88
<212> TYPE: PRT
<213> ORGANISM: Bacteriophage Tuc2009

<400> SEQUENCE: 12

Met Asn Gln Ile Asn Trp Lys Leu Arg Leu Lys Ser Lys Ala Phe Trp
1               5                   10                  15

Leu Ala Leu Leu Pro Ala Leu Phe Leu Leu Ile Gln Ala Ile Gly Ala
            20                  25                  30

Pro Phe Gly Tyr Lys Trp Asp Phe Val Ile Leu Asn Gln Gln Leu Ala
        35                  40                  45

Ala Val Val Asn Ala Ala Phe Ala Leu Leu Ala Ile Val Gly Val Val
    50                  55                  60

Ala Asp Pro Thr Thr Ser Gly Leu Gly Asp Ser Asp Arg Val Leu Asn
65                  70                  75                  80

Lys Asp Lys Ser Glu Glu Asn Lys
                85

<210> SEQ ID NO 13
<211> LENGTH: 88
<212> TYPE: PRT
<213> ORGANISM: Bacteriophage TPW22

<400> SEQUENCE: 13

Met Asn Gln Ile Asn Trp Lys Leu Arg Leu Lys Ser Lys Ala Phe Trp
1               5                   10                  15

Leu Ala Leu Leu Pro Ala Leu Phe Leu Leu Ile Gln Ala Ile Gly Ala
            20                  25                  30

Ser Phe Gly Tyr Lys Trp Asn Phe Val Ile Leu Asn Gln Gln Leu Ala
        35                  40                  45

Ala Val Val Asn Ala Ala Phe Ala Leu Leu Ala Ile Val Gly Val Val
    50                  55                  60

Ala Asp Pro Thr Thr Ser Gly Leu Gly Asp Ser Asp Arg Val Leu Asn
65                  70                  75                  80

Lys Asp Lys Ser Glu Glu Asn Lys
                85

<210> SEQ ID NO 14
<211> LENGTH: 74
<212> TYPE: PRT
<213> ORGANISM: Artificial Sequence
<220> FEATURE:
<223> OTHER INFORMATION: Synthetic Construct

<400> SEQUENCE: 14

```
Met Arg Phe Asn Met Leu Lys Asn Ser Glu Thr Thr Gly Ala Tyr Val
1               5                   10                  15

Gly Ser Ala Ile Ala Ile Tyr Ser Gly Phe Thr Leu Ala Asp Trp Ala
            20                  25                  30

Ala Ile Phe Gly Ile Leu Phe Gly Leu Phe Thr Met Leu Ile Asn Trp
            35                  40                  45

Tyr Tyr Lys Asn Lys Glu Ile Lys Leu Lys Gly Thr Ala Leu Lys Gln
    50                  55                  60

Lys Ile Asp Leu Lys Glu Gly Asp His Glu
65                  70
```

<210> SEQ ID NO 15
<211> LENGTH: 133
<212> TYPE: PRT
<213> ORGANISM: Bacillus phage GA-1

<400> SEQUENCE: 15

```
Met Phe Glu Phe Phe His Ser Leu Met Glu Thr Asp Asp Thr Lys Val
1               5                   10                  15

Tyr Phe Leu Leu Gly Ile Ile Gly Val Leu Asn Ile Val Asp Phe Phe
            20                  25                  30

Phe Gly Phe Ile Asn Ala Lys Phe Asn Lys Ser Ile Ala Tyr Lys Ser
            35                  40                  45

Ser Lys Thr Ile Asp Gly Ile Met Arg Lys Met Lys Phe Thr Ile Met
    50                  55                  60

Ala Ile Leu Phe Ile Pro Val Ser Val Leu Met Pro Glu Pro Ile Gly
65                  70                  75                  80

Leu Gly Ala Leu Tyr Val Phe Tyr Phe Gly Tyr Ile Tyr Ala Glu Leu
                85                  90                  95

Asn Ser Ile Leu Ser His Leu Lys Leu Ser Glu Asp Gly Lys Glu Thr
            100                 105                 110

Glu Val Phe Leu Asp Phe Ile Asn Thr Phe Phe Asn Ser Thr Lys Gly
            115                 120                 125

Asp Lys Lys Asp Asp
        130
```

<210> SEQ ID NO 16
<211> LENGTH: 57
<212> TYPE: PRT
<213> ORGANISM: Staphylococcus phage 187

<400> SEQUENCE: 16

```
Met Leu Met Val Ile Met Val Gly Asn Val Gly Ile Tyr Leu Thr Ile
1               5                   10                  15

Phe Leu Ile Asp Thr Gly Thr Leu Arg His Gln Ala Thr Gln Glu Ile
            20                  25                  30

Trp His Gly Ile Asp Ile Leu Lys Gly Leu Lys Cys Leu Glu Thr Leu
            35                  40                  45

Leu Ile Leu Ser Leu Asn Gln Val Ile
    50                  55
```

<210> SEQ ID NO 17
<211> LENGTH: 71
<212> TYPE: PRT
<213> ORGANISM: Shigella dysenteriae

<400> SEQUENCE: 17

```
Met Tyr Gln Met Glu Lys Ile Thr Thr Gly Val Ser Tyr Thr Thr Ser
```

-continued

```
                 1               5                   10                  15
Ala Val Gly Met Gly Tyr Trp Phe Leu Gln Phe Leu Asp Arg Val Ser
                20                  25                  30

Pro Ser Gln Trp Ala Ala Ile Gly Val Leu Gly Ser Leu Leu Phe Gly
            35                  40                  45

Leu Leu Thr Tyr Leu Thr Asn Leu Tyr Phe Lys Ile Arg Glu Asp Arg
        50                  55                  60

Arg Lys Ala Ala Arg Gly Glu
65                  70

<210> SEQ ID NO 18
<211> LENGTH: 75
<212> TYPE: PRT
<213> ORGANISM: Artificial Sequence
<220> FEATURE:
<223> OTHER INFORMATION: Synthetic Construct

<400> SEQUENCE: 18

Met Glu Arg Trp Thr Leu Leu Asp Ile Leu Ala Phe Leu Leu Leu Leu
1               5                   10                  15

Ser Leu Leu Leu Pro Ser Leu Leu Ile Met Phe Ile Pro Ser Met Tyr
                20                  25                  30

Lys Gln His Ala Ser Leu Trp Lys Ala Arg Ser Leu Ala Lys Thr Leu
            35                  40                  45

Ser Met Ala Ser Ser Ala Arg Leu Thr Pro Leu Ser Ser Ser Arg Thr
        50                  55                  60

Pro Cys Val Leu Lys Gln Asp Ser Lys Lys Leu
65                  70                  75

<210> SEQ ID NO 19
<211> LENGTH: 87
<212> TYPE: PRT
<213> ORGANISM: B.subtilis

<400> SEQUENCE: 19

Met Asn Thr Phe Asp Lys Gly Thr Val Ile Arg Thr Val Leu Leu Leu
1               5                   10                  15

Ile Ala Leu Ile Asn Gln Thr Met Leu Met Leu Gly Lys Ser Pro Leu
                20                  25                  30

Asp Ile Gln Glu Glu Gln Val Asn Gln Leu Ala Asp Ala Leu Tyr Ser
            35                  40                  45

Ala Gly Ser Ile Ala Phe Thr Ile Gly Thr Leu Ala Ala Trp Phe
        50                  55                  60

Lys Asn Asn Tyr Val Thr Glu Lys Gly Lys Gln Arg Asp Leu Leu
65                  70                  75                  80

Arg Asp Asn Asn Leu Thr Lys
                85

<210> SEQ ID NO 20
<211> LENGTH: 70
<212> TYPE: PRT
<213> ORGANISM: Bacillus subtilis 168 prophage

<400> SEQUENCE: 20

Met Glu Met Asp Ile Thr Gln Tyr Leu Ser Thr Gln Gly Pro Phe Ala
1               5                   10                  15

Val Leu Phe Cys Trp Leu Leu Phe Tyr Val Met Lys Thr Ser Lys Glu
                20                  25                  30
```

Arg Glu Ser Lys Leu Tyr Asn Gln Ile Asp Ser Gln Asn Glu Val Leu
            35                  40                  45

Gly Lys Phe Ser Glu Lys Tyr Asp Val Val Ile Glu Lys Leu Asp Lys
 50                  55                  60

Ile Glu Gln Asn Phe Lys
 65                  70

<210> SEQ ID NO 21
<211> LENGTH: 88
<212> TYPE: PRT
<213> ORGANISM: Bacillus subtilis 168 prophage

<400> SEQUENCE: 21

Met Phe Glu Asn Ile Asp Lys Gly Thr Ile Val Arg Thr Leu Leu Leu
 1               5                  10                  15

Ala Ile Ala Leu Leu Asn Gln Ile Met Val Met Leu Gly Lys Ala Ala
            20                  25                  30

Phe Ile Ile Asn Glu Glu Asp Ile Asn His Leu Tyr Asp Cys Leu Tyr
            35                  40                  45

Thr Ile Phe Thr Ile Val Phe Thr Thr Ser Thr Thr Ala Ala Trp
 50                  55                  60

Phe Lys Asn Asn Tyr Ile Thr Ala Lys Gly Lys Lys Gln Lys Gln Val
 65                  70                  75                  80

Leu Lys Lys Glu Asn Leu Phe Lys
                85

<210> SEQ ID NO 22
<211> LENGTH: 119
<212> TYPE: PRT
<213> ORGANISM: Bacteriophage phi-Ea1h

<400> SEQUENCE: 22

Met Arg Lys Ile Tyr Val Val Ile Ile Thr Thr Ile Val Val Ala Gly
 1               5                  10                  15

Leu Ile Trp Ala Phe Ile Ala Thr Gln Val Asn Thr Gly Val Thr Ser
            20                  25                  30

Lys Arg Gln Glu Asp Ala Leu Ala Val Ser Glu Ala Asn Val Gly Ile
            35                  40                  45

Gly Lys Glu Ala Lys Asp Gln Gly Glu Gln Ala Thr Lys Arg Ala Asp
 50                  55                  60

Val Ala Lys Glu Gln Arg Thr His Gln Ile Asn Gln Leu Lys Asp Lys
 65                  70                  75                  80

Leu His Glu Lys Ala Glu Ser Tyr Asp Ser Ile Pro Leu Ser Pro Ser
                85                  90                  95

Asp Val Asp Ile Leu Cys Arg Ala Tyr Arg Ser Thr Asp Pro Val Cys
            100                 105                 110

Ser Pro Thr Val Lys Ser Asp
            115

<210> SEQ ID NO 23
<211> LENGTH: 91
<212> TYPE: PRT
<213> ORGANISM: Phage phiX174

<400> SEQUENCE: 23

Met Val Arg Trp Thr Leu Trp Asp Thr Leu Ala Phe Leu Leu Leu Leu
 1               5                  10                  15

Ser Leu Leu Leu Pro Ser Leu Leu Ile Met Phe Ile Pro Ser Thr Phe

```
                20                  25                  30
Lys Arg Pro Val Ser Ser Trp Lys Ala Leu Asn Leu Arg Lys Thr Leu
            35                  40                  45

Leu Met Ala Ser Ser Val Arg Leu Lys Pro Leu Asn Cys Ser Arg Leu
 50                  55                  60

Pro Cys Val Tyr Ala Gln Glu Thr Leu Thr Phe Leu Leu Thr Gln Lys
 65                  70                  75                  80

Lys Thr Cys Val Lys Asn Tyr Val Gln Lys Glu
                85                  90

<210> SEQ ID NO 24
<211> LENGTH: 109
<212> TYPE: PRT
<213> ORGANISM: Artificial Sequence
<220> FEATURE:
<223> OTHER INFORMATION: Synthetic Construct

<400> SEQUENCE: 24

Met Pro Cys Leu Ile His Leu Val Gly Trp Gly Ser Ser Pro Gly Ser
 1               5                  10                  15

Ala Leu Ile Arg Glu Gln Ala Ile Gly Ala Gly Leu Ala Ala Trp Met
            20                  25                  30

Thr Cys Leu Arg Gly Arg Tyr Leu Gly Arg Gly Trp Arg Lys Thr Thr
        35                  40                  45

Phe Asp Ala Ala Ile Cys Ala Leu Ile Ala Trp Phe Ala Arg Asp Gly
 50                  55                  60

Leu Ala Leu Val Gly Ile Asp Asn Gln Phe Ser Tyr Leu Ser Ser Ile
 65                  70                  75                  80

Ile Val Gly Tyr Leu Gly Asn Asp Tyr Leu Gly Ala Leu Leu Arg Arg
                85                  90                  95

Arg Leu Glu Lys Lys Ser Gly Glu Ser Asn Ala Pro Gln
            100                 105

<210> SEQ ID NO 25
<211> LENGTH: 95
<212> TYPE: PRT
<213> ORGANISM: Listeria innocua

<400> SEQUENCE: 25

Met Met Lys Met Glu Phe Gly Lys Glu Leu Leu Val Tyr Met Thr Phe
 1               5                  10                  15

Leu Val Val Val Thr Pro Val Phe Val Gln Ala Ile Lys Lys Thr Glu
            20                  25                  30

Leu Ile Pro Ser Lys Trp Leu Pro Thr Val Ser Ile Leu Val Gly Ala
        35                  40                  45

Ile Leu Gly Ala Leu Ala Thr Ser Leu Asp Gly Ser Gly Ser Leu Ala
 50                  55                  60

Thr Met Ile Trp Ala Gly Ala Leu Ala Gly Ala Gly Thr Gly Leu
 65                  70                  75                  80

Phe Glu Gln Phe Thr Asn Arg Ala Lys Lys Tyr Gly Lys Asp Asp
                85                  90                  95

<210> SEQ ID NO 26
<211> LENGTH: 145
<212> TYPE: PRT
<213> ORGANISM: Bacteriophage 80 alpha

<400> SEQUENCE: 26
```

-continued

```
Met Asp Ile Asn Trp Lys Leu Arg Phe Lys Asn Lys Ala Val Leu Thr
1               5                   10                  15

Gly Leu Val Gly Ala Leu Phe Val Phe Ile Lys Gln Val Thr Asp Leu
            20                  25                  30

Phe Gly Leu Asp Leu Ser Thr Gln Leu Asn Gln Ala Ser Ala Ile Ile
        35                  40                  45

Gly Ala Ile Leu Thr Leu Leu Thr Gly Ile Gly Val Ile Thr Asp Pro
    50                  55                  60

Thr Ser Lys Gly Val Ser Asp Ser Ser Ile Ala Gln Thr Tyr Gln Ala
65                  70                  75                  80

Pro Arg Asp Ser Lys Lys Glu Glu Gln Gln Val Thr Trp Lys Ser Ser
                85                  90                  95

Gln Asp Ser Ser Leu Thr Pro Glu Leu Ser Ala Lys Ala Pro Lys Glu
            100                 105                 110

Tyr Asp Thr Ser Gln Pro Phe Thr Asp Ala Ser Asn Asp Val Gly Phe
        115                 120                 125

Asp Val Asn Glu Tyr His His Gly Gly Gly Asp Asn Ala Ser Lys Ile
    130                 135                 140

Asn
145

<210> SEQ ID NO 27
<211> LENGTH: 145
<212> TYPE: PRT
<213> ORGANISM: Staphylococcus bacteriophage phi 11

<400> SEQUENCE: 27

Met Asp Ile Asn Trp Lys Leu Arg Phe Lys Asn Lys Ala Val Leu Thr
1               5                   10                  15

Gly Leu Val Gly Ala Leu Phe Val Phe Ile Lys Gln Val Thr Asp Leu
            20                  25                  30

Phe Gly Leu Asp Leu Ser Thr Gln Leu Asn Gln Ala Ser Ala Ile Ile
        35                  40                  45

Gly Ala Ile Leu Thr Leu Leu Thr Gly Ile Gly Val Ile Thr Asp Pro
    50                  55                  60

Thr Ser Lys Gly Val Ser Asp Ser Ser Ile Ala Gln Thr Tyr Gln Ala
65                  70                  75                  80

Pro Arg Asp Ser Lys Lys Glu Glu Gln Gln Val Thr Trp Lys Ser Ser
                85                  90                  95

Gln Asp Ser Ser Leu Thr Pro Glu Leu Ser Ala Lys Ala Pro Lys Glu
            100                 105                 110

Tyr Asp Thr Ser Gln Pro Phe Thr Asp Ala Ser Asn Asp Val Gly Phe
        115                 120                 125

Asp Val Asn Glu Tyr His His Gly Gly Gly Asp Asn Ala Ser Lys Ile
    130                 135                 140

Asn
145

<210> SEQ ID NO 28
<211> LENGTH: 138
<212> TYPE: PRT
<213> ORGANISM: Streptococcus pneumoniae bacteriophage MM1

<400> SEQUENCE: 28

Met Lys Ile Glu Phe Phe Asn Phe Leu Arg Ser Val Ile Gln Thr Glu
1               5                   10                  15
```

```
Asp Gly Leu Val Leu Tyr Ala Leu Ala Leu Ile Val Ser Met Glu Ile
            20                  25                  30

Ile Asp Phe Val Thr Gly Thr Ile Ala Ala Ile Ile Asn Pro Asp Ile
        35                  40                  45

Glu Tyr Lys Ser Lys Ile Gly Ile Asn Gly Leu Leu Arg Lys Ile Ser
    50                  55                  60

Gly Val Leu Leu Leu Met Ile Leu Ile Pro Ala Ser Val Leu Leu Pro
65                  70                  75                  80

Glu Lys Thr Gly Phe Ala Phe Leu Tyr Ser Ile Cys Leu Gly Tyr Ile
                85                  90                  95

Ala Phe Thr Phe Gln Ser Leu Ile Glu Asn Tyr Arg Lys Leu Lys Gly
            100                 105                 110

Asn Val Thr Leu Phe Gln Pro Ile Val Lys Val Phe Gln Arg Leu Leu
        115                 120                 125

Glu Lys Asp Asp Asp Thr Lys Lys Gly Glu
    130                 135

<210> SEQ ID NO 29
<211> LENGTH: 86
<212> TYPE: PRT
<213> ORGANISM: Streptococcus thermophilus bacteriophage Sfi21

<400> SEQUENCE: 29

Met Lys Lys Arg Lys Lys Lys Met Ile Asn Phe Lys Leu Arg Leu Gln
1               5                   10                  15

Asn Lys Ala Thr Leu Val Ala Leu Ile Ser Ala Val Phe Leu Met Leu
            20                  25                  30

Gln Gln Phe Gly Leu His Val Pro Asn Asn Ile Gln Gly Ile Asn Thr
        35                  40                  45

Leu Val Gly Ile Leu Val Ile Leu Gly Ile Ile Thr Asp Pro Thr Thr
    50                  55                  60

Lys Gly Ile Ala Asp Ser Glu Arg Ala Leu Ser Tyr Ile Gln Pro Leu
65                  70                  75                  80

Asp Asp Lys Glu Val Tyr
                85

<210> SEQ ID NO 30
<211> LENGTH: 96
<212> TYPE: PRT
<213> ORGANISM: Bacteriophage A500

<400> SEQUENCE: 30

Met Met Lys Met Glu Phe Gly Lys Glu Leu Leu Val Tyr Met Thr Phe
1               5                   10                  15

Leu Val Val Val Thr Pro Val Phe Val Gln Ala Ile Lys Lys Thr Glu
            20                  25                  30

Leu Ile Pro Ser Lys Trp Leu Pro Thr Val Ser Ile Leu Val Gly Ala
        35                  40                  45

Ile Leu Gly Ala Leu Ala Thr Ser Leu Asp Gly Ser Gly Ser Leu Ala
    50                  55                  60

Thr Met Ile Trp Ala Gly Ala Leu Ala Gly Ala Gly Thr Gly Leu
65                  70                  75                  80

Phe Glu Gln Phe Thr Asn Arg Ala Lys Lys Tyr Gly Lys Asp Asp Lys
                85                  90                  95

<210> SEQ ID NO 31
<211> LENGTH: 90
```

```
<212> TYPE: PRT
<213> ORGANISM: Bacteriophage PL-1

<400> SEQUENCE: 31

Met Gln Asn Glu Leu Leu Gln Val Leu Ala Ile Ala Phe Val Ile Ala
1               5                   10                  15

Pro Ile Thr Thr Gly Phe Thr Glu Ile Phe Lys Arg Tyr Thr Pro Ala
            20                  25                  30

Glu Gly Lys Leu Leu Pro Val Leu Ser Ile Gly Thr Gly Ile Leu Leu
        35                  40                  45

Ala Cys Val Trp Ala Met Ala Phe Gly His Leu Pro Leu Ile Gly Ala
    50                  55                  60

Tyr Ala Leu Ala Gly Met Leu Ser Gly Leu Ala Ser Val Gly Val Tyr
65                  70                  75                  80

Gln Ile Val Lys Pro Asn Glu Glu Val Lys
                85                  90
```